(12) United States Patent
Yang et al.

(10) Patent No.: US 11,875,503 B2
(45) Date of Patent: Jan. 16, 2024

(54) METHOD AND SYSTEM FOR MEASURING MORPHOLOGICAL PARAMETERS OF AN INTRACRANIAL ANEURYSM IMAGE

(71) Applicant: Union Strong (Beijing) Technology Co. Ltd., Beijing (CN)

(72) Inventors: Guangming Yang, Beijing (CN); Wenzhi Wang, Beijing (CN); Xue Feng, Charlottesville, VA (US); Ling Song, Beijing (CN); Lan Qin, Beijing (CN)

(73) Assignee: UNION STRONG (BEIJING) TECHNOLOGY CO. LTD., Beijing (CN)

( * ) Notice: Subject to any disclaimer, the term of this patent is extended or adjusted under 35 U.S.C. 154(b) by 402 days.

(21) Appl. No.: 15/734,521

(22) PCT Filed: Oct. 25, 2019

(86) PCT No.: PCT/CN2019/113269
§ 371 (c)(1),
(2) Date: Dec. 2, 2020

(87) PCT Pub. No.: WO2020/083375
PCT Pub. Date: Apr. 30, 2020

(65) Prior Publication Data
US 2021/0272274 A1 Sep. 2, 2021

(30) Foreign Application Priority Data

Oct. 26, 2018 (CN) .......................... 201811260200.5

(51) Int. Cl.
*G06T 7/00* (2017.01)
*G06T 7/11* (2017.01)
*G16H 30/20* (2018.01)

(52) U.S. Cl.
CPC .............. *G06T 7/0012* (2013.01); *G06T 7/11* (2017.01); *G16H 30/20* (2018.01); *G06T 2207/20156* (2013.01); *G06T 2207/30101* (2013.01)

(58) Field of Classification Search
CPC ..................... G06T 7/0012; G06T 7/11; G06T 2207/20156; G06T 2207/30101;
(Continued)

(56) References Cited

U.S. PATENT DOCUMENTS 5,978,562 A * 11/1999 Sako .................. H04N 1/32358
358/1.16
9,830,427 B2 * 11/2017 Baloch .................. G16H 50/50
(Continued)

FOREIGN PATENT DOCUMENTS

CN 107049484 A 8/2017
CN 107847207 A 3/2018
(Continued)

*Primary Examiner* — Lewis G West
(74) *Attorney, Agent, or Firm* — The PL Law Group, PLLC

(57) ABSTRACT

A method and a system for measuring morphological parameters of an intracranial aneurysm image, the method comprises: segmenting an intracranial parent artery image from three-dimensional DICOM data of DSA (S101); segmenting the intracranial aneurysm image on the intracranial aneurysm image (S102); and measuring morphological parameters of the intracranial aneurysm image (S103). The method and the system for measuring the morphological parameters of the intracranial aneurysm image as disclosed may implement automated measurement of the intracranial aneurysm image, quickly measure morphological parameters of the intracranial aneurysm image, and guarantee consistency between measurements of morphological parameters of the aneurysm image.

4 Claims, 5 Drawing Sheets

(58) Field of Classification Search
CPC . G06T 2207/10116; G06T 2207/30172; G06T 7/62; G06T 17/00; G06T 2207/30096; G16H 30/20
See application file for complete search history.

(56) References Cited

U.S. PATENT DOCUMENTS

| | | | |
|---|---|---|---|
| 2003/0053697 A1* | 3/2003 | Aylward | G06T 7/64 382/203 |
| 2009/0214097 A1 | 8/2009 | Mohamed | |
| 2009/0297004 A1* | 12/2009 | Baumgart | G16H 20/17 382/130 |
| 2012/0041739 A1* | 2/2012 | Taylor | G16B 5/00 703/11 |
| 2012/0323547 A1* | 12/2012 | Baloch | G16H 50/50 703/11 |
| 2015/0302007 A1* | 10/2015 | Sitka | G06F 16/214 707/602 |
| 2018/0182132 A1* | 6/2018 | Kowarschik | A61B 6/504 |
| 2018/0204339 A1* | 7/2018 | Yoneyama | A61B 6/03 |
| 2021/0228275 A1* | 7/2021 | Song | A61B 34/10 |
| 2023/0237654 A1* | 7/2023 | Min | A61B 5/055 382/131 |

FOREIGN PATENT DOCUMENTS

| | | |
|---|---|---|
| CN | 109345585 A | 2/2019 |
| CN | 109472823 A | 3/2019 |
| CN | 109493348 A | 3/2019 |
| DE | 102010041619 A1 | 3/2012 |
| JP | 2011104206 A | 6/2011 |

* cited by examiner

METHOD AND SYSTEM FOR MEASURING MORPHOLOGICAL PARAMETERS OF AN INTRACRANIAL ANEURYSM IMAGE

CROSS REFERENCE TO RELATED APPLICATIONS

This application is a national stage application under 35 U.S.C. § 371 of International Application No. PCT/CN2019/113269, filed internationally on Oct. 25, 2019 which claims the benefit of Chinese Application No. 201811260200.5, filed Oct. 26, 2018, the contents of which are incorporated herein by reference in their entirety.

FIELD

The present disclosure relates to medical images, and more particularly relates to a method and a system for measuring morphological parameters of an intracranial aneurysm image.

BACKGROUND

An intracranial aneurysm is a protuberance on an arterial wall caused by abnormal localized dilation of an intracranial arterial lumen, which is a common vascular disease. As reported, unruptured intracranial aneurysms occur in as high as 7% of the adults in China. Aneurysm rupture results in subarachnoid hemorrhage (SAH), potentially leading to catastrophic disabilities or even death. 2014 statistics released by the National Bureau of Statistics showed that acute cerebrovascular diseases ranked as the second leading cause of death in the population of China. Aneurysmal subarachnoid hemorrhage (aSAH) is one of the most common acute cerebrovascular diseases after cerebral ischemic stroke (CIS) and hypertensive intracerebral hemorrhage (HICH). The aSAH death and disability rate is up to 64% and the DOA (Death on Arrival) is about 15%; therefore, aSAH has become one of the most common causes of death in Chinese population. However, the aSAH treatment and cure levels differ greatly between regions with different economic development levels. Therefore, timely and effective screening and forestalling of unruptured intracranial aneurysms can reduce the risk of future occurrence to aneurysms-suffering patients to a greater extent.

In the prior art, intracranial aneurysm images were basically measured manually by experienced physicians with the aid of computers, featuring a slow measurement speed, inconsistent measurements, and an undesired preciseness. Besides, the conventional approach can only measure simple parameters, e.g., segment distance. For complex parameters, e.g., volume or angle, the conventional manual measurement manners become very unwieldy without a guaranteed preciseness. Traditional improvements were mainly directed to model simulation or manual measurement manners, which cannot implement fully-automated measurement of aneurysm morphological parameters and hence cannot guarantee consistency of measurements.

Therefore, an automated method for measuring morphological parameters of an intracranial aneurysm image is desired, which should be capable of quickly measuring morphological parameters of the intracranial aneurysm image.

SUMMARY

Embodiments of the present disclosure provide an automated method for measuring morphological parameters of an intracranial aneurysm image and a corresponding method so as to quickly measure morphological parameters of the intracranial aneurysm image and guarantee consistency of measurements.

To achieve objectives of the present disclosure, embodiments of the present disclosure are implemented as such:

A method for measuring morphological parameters of an intracranial aneurysm image comprises:

segmenting an intracranial parent artery image from three-dimensional DICOM data of DSA;

segmenting the intracranial aneurysm image on the intracranial parent artery image; and measuring morphological parameters of the intracranial aneurysm image.

Further, a seed point on the three-dimensional DICOM data of the DSA is automatically selected to segment the intracranial parent artery image.

Further, the centerline and the radius of the parent artery are computed on the intracranial parent artery image to segment the intracranial aneurysm image.

Further, the aneurysm neck is generated using the segmented intracranial aneurysm image to measure the morphological parameters of the intracranial aneurysm image.

A system for measuring morphological parameters of an intracranial aneurysm image comprises:

an input interface configured for inputting three-dimensional DICOM data of DSA;

a processing workstation configured for measuring the morphological parameters for the intracranial aneurysm image; and an output unit configured for outputting measurements of the morphological parameters of the intracranial aneurysm image.

Further, an intracranial parent artery image is segmented from the three-dimensional DICOM data of DSA;

the intracranial aneurysm image is segmented on the intracranial parent artery image; and the morphological parameters of the intracranial aneurysm image are measured.

Further, a seed point on the three-dimensional DICOM data of the DSA is automatically selected to segment the intracranial parent artery image.

Further, the centerline and the radius of the parent artery are computed to segment the intracranial aneurysm image on the intracranial parent artery image.

Further, the aneurysm neck is generated using the segmented intracranial aneurysm image to measure the morphological parameters of the intracranial aneurysm image.

At least one of the technical solutions as adopted in the embodiments of the present disclosure may achieve the following effects: based on the three-dimensional DICOM data of DSA, the embodiments of the present disclosure realize automated measurement of morphological parameters of the intracranial aneurysm image, enable quick measurement of the morphological parameters of the intracranial aneurysm image, and guarantee consistency of the measurements.

BRIEF DESCRIPTION OF THE DRAWINGS

To elucidate the technical solutions of the present disclosure or the prior art, the drawings used in describing the embodiments of the present disclosure or the prior art will be briefly introduced below. It is understood that the drawings as described only relate to some embodiments of the present disclosure. To those skilled in the art, other drawings may be derived based on these drawings without exercise of inventive work, wherein.

DETAILED DESCRIPTION OF EMBODIMENTS

To facilitate those skilled in the art to better understand the technical solutions of the present disclosure, the technical solutions of the present disclosure will be described in a clear and complete manner with reference to the accompanying drawings; it is apparent that the embodiments described hereon are only part of the embodiments of the present disclosure, rather all of them. All other embodiments obtained by those skilled in the art without exercise of inventive work based on the embodiments in the present disclosure shall fall within the protection scope of the present disclosure.

Figure 1:
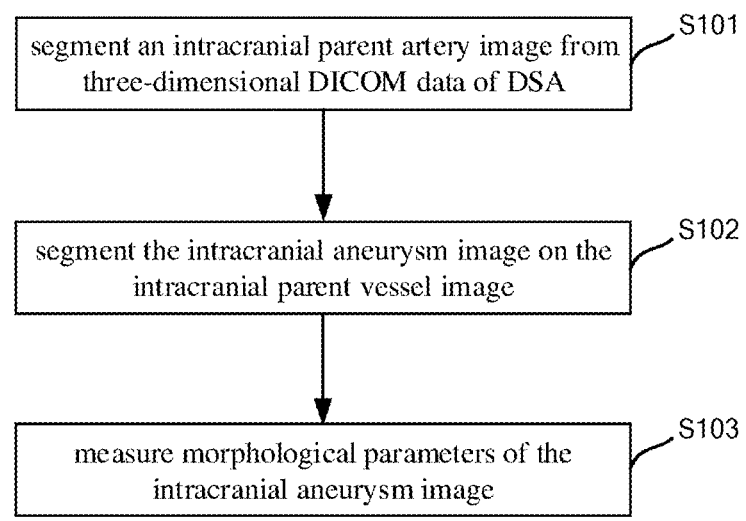
FIG. 1 shows a flow diagram of a method for measuring morphological parameters of an intracranial aneurysm image according to the present disclosure.

FIG. 1 shows a flow diagram of a method for measuring morphological parameters of an intracranial aneurysm image according to the present disclosure. The method comprises:

Step S101: segmenting an intracranial parent artery image from three-dimensional DICOM data of DSA.

The morphological parameters of the intracranial aneurysm image are usually measured using three-dimensional DICOM (Digital Imaging and Communications in Medicine) data of the intracranial aneurysm DSA (Digital Subtraction Angiography). DSA is a technique to visualize a blood vessel in a sequence of X-ray images. Its fundamental principle is to digitalize two frames of an X-ray image, which are captured before and after injecting the contrast medium, respectively, and input the digitalized images into an image computer, then through processes of subtraction, enhancement, and re-imaging, obtain a clear pure vessel image, and meanwhile present the angiogram in real time. Due to its advantages of high-contrast resolution, short examination time, low dose and low concentration of contrast agents, significant reduction of X-ray adsorption in the patient, and less film to use, etc., the DSA plays a significant role in clinic diagnosis of vascular diseases. The DSA technique is acclaimed as gold standard for diagnosing vascular diseases due to its superiority over other examination means in aspects of image quality, blood flow direction determination, and preponderant blood feeding.

DICOM is a network communications interface standard for digital medical images. The DICOM standard is a set of protocols to be followed by devices claiming conformance to the Standard; the syntax and semantics of Commands and associated information that can be exchanged using these protocols between different devices and systems. The main objective of the protocols is to guarantee communications between different devices and systems with respect to a patient's diagnosis information, treatment information, medical images, and various other relevant data.

The DSA image is stored in a DICOM-format file. The DICOM-format file not only includes essential information of typical images such as image size, height, width, number of bytes per pixel, buts also store, in data elements of a data set, detailed medical information such as patient name, age, hospital name, imaging time, examined part, etc. The DICOM data are stored in sequence, where the first byte in the array represents the pixel at the upper left corner of the image, while the last byte represents the pixel at the lower right corner of the image.

Due to limitation of device irradiation azimuth, the intracranial aneurysm DSA can only be rendered two-dimensionally. The two-dimensional image can only capture basic morphological parameter indexes of the intracranial aneurysm image: size, aspect ratio, and inclination angle of the aneurysm, etc., such that it is unable to measure complex morphological parameters of the intracranial aneurysm image, e.g., the volume of the aneurysm. However, measurements of three-dimensional morphological parameters are more significant to study morphological parameters of the intracranial aneurysm image. Therefore, to measure the morphological parameters of the intracranial aneurysm image, the three-dimensional DICOM data of the DSA need to be further processed. First, an intracranial parent artery image should be segmented.

Figure 2:
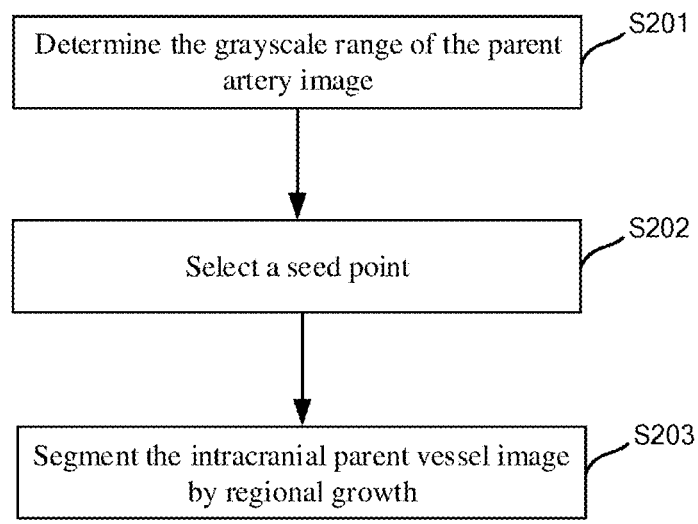
FIG. 2 shows a flow diagram of segmenting an intracranial parent artery image according to the present disclosure.

FIG. 2 shows a flow diagram of segmenting the intracranial parent artery image according to the present disclosure. The specific process includes:

Step S201: determining a grayscale range of the patent vessel image.

According to imaging characteristics of three-dimensional DSA images, a relatively broad grayscale threshold may be obtained based on the range of the pixel value of the DSA image while accounting for the simple maximum constraint and the minimum value constraint, wherein such grayscale thresholds serve as the grayscale range.

Specifically, the value range of the three-dimensional DSA image is extracted to obtain the maximum value and the minimum value; then the sum of the maximum value and twice the minimum value are trisected. The trisection value serves as the minimum grayscale range, while the maximum grayscale range is selected as the maximum value of the range.

Because the DSA image proper has a good quality, the grayscale range may also be obtained by other means, e.g., extracting the value range of the three-dimensional DSA image to obtain the maximum value and the minimum value; then quartering the maximum value and the sum of the maximum value and three times the minimum value; the quarter value serves as the minimum grayscale range, while the maximum grayscale range is selected as the maximum value of the range.

Step S202: selecting a seed point.

The seed point herein is defined as a growing start point. The seed point is the start point for subsequent region growing.

In an embodiment of the present disclosure, the three-dimensional image space of the entire DSA is traversed to find the pixel point with the largest grayscale value, the coordinates of the pixel point being marked out as coordinates of the seed point. The seed point is located on a parent artery image of the intracranial aneurysm.

Step 203: segmenting the intracranial parent artery image by region growing.

With the point with the maximum grayscale as the seed point, the intracranial parent artery image is automatically segmented through point-by-point computation and determination by region growing. This method may effectively reduce noise interference and enhance operational efficiency.

Step S102: segmenting the intracranial aneurysm image.

The segmented intracranial parent artery image needs to be further segmented to thereby implement segmentation of the aneurysm image on the intracranial parent artery image, thereby obtaining the segmented intracranial aneurysm image.

Figure 3:
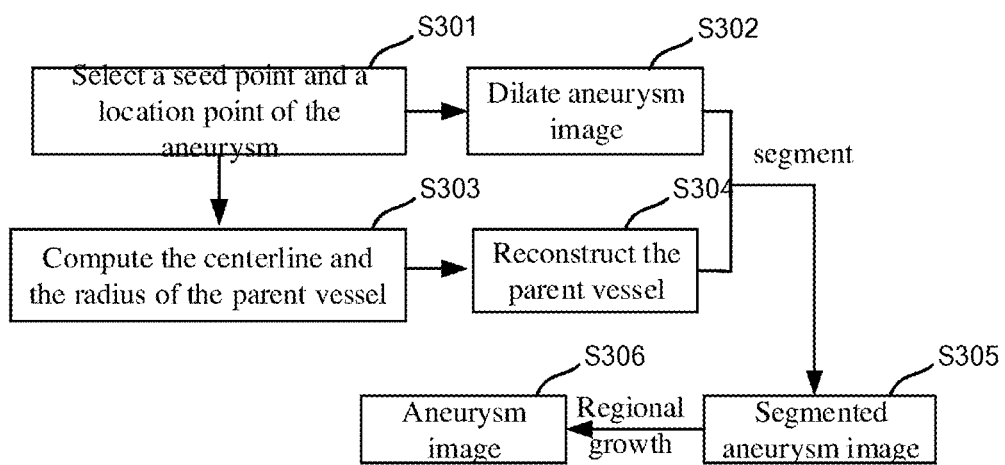
FIG. 3 shows a flow diagram of segmenting an intracranial aneurysm image according to the present disclosure.

FIG. 3 shows a flow diagram of segmenting an intracranial aneurysm image according to the present disclosure. The method comprises:

Step S301: selecting a seed point and a location point on the to-be-segmented intracranial parent artery image.

A seed point and a location point are selected using the obtained intracranial parent artery image. The seed point and the location point are both spatial coordinates. To facilitate discrimination, the start point of growing is defined as the seed point, while a point selected on the parent artery is defined as the location point. The seed point may be selected either on the surface of the aneurysm body or in the aneurysm body. The location point is selected on the parent artery intersected with the aneurysm. Because intracranial aneurysms include typical side aneurysms and bifurcation aneurysms, the location point should be selected dependent on the type of the intracranial aneurysm. For a typical side aneurysm, it is only needed to select two points respectively upstream and downstream of the parent artery. Generally, two points within a range of 5~10 mm distant from the aneurysm are selected; for a bifurcation aneurysm, it is needed to select one location point upstream of the parent artery and one location point respectively from each of the downstream bifurcations, i.e., three location points in total. Particularly, the upstream location point is marked as location point 1 and the downstream location point is marked as location point 2; for the bifurcation vessel, there are two downstream location points. The location points may be disposed either on the surface of the parent artery or in the parent artery, without any discrimination therebetween.

Step S302: performing image dilation using the seed point and the location point to generate a dilated aneurysm image.

A minimum containing cuboid is determined based on the selected seed point and location points. The determined minimum containing cuboid is subjected to transverse and longitudinal incremental extension of pixels, such that the extended cuboid may cover the entire intracranial aneurysm image; a local three-dimensional image is cropped using the extended cuboidal region. Although the local three-dimensional image covers the entire intracranial aneurysm image, due to the impact of noise, the local three-dimensional image does not facilitate subsequent segmentation of the aneurysm image; therefore, it needs to be subjected to further image dilation. With the seed point as the start point, after the local image is dilated for 16 times, the generated aneurysm may be used for subsequent segmentation of aneurysm image.

Figure 4:
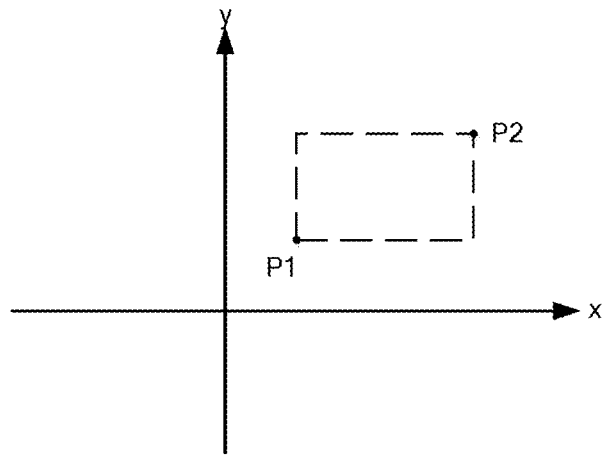
FIG. 4 shows a schematic diagram of determining a minimum containing rectangle (MCR) based on two points in a two-dimensional space according to the present disclosure.

FIG. 4 shows a schematic diagram of determining a minimum containing rectangle based on two points in a two-dimensional space according to the present disclosure. Following a similar method, a minimum containing cuboid is determined in the three-dimensional space based on two location points and one seed point.

Figure 5:
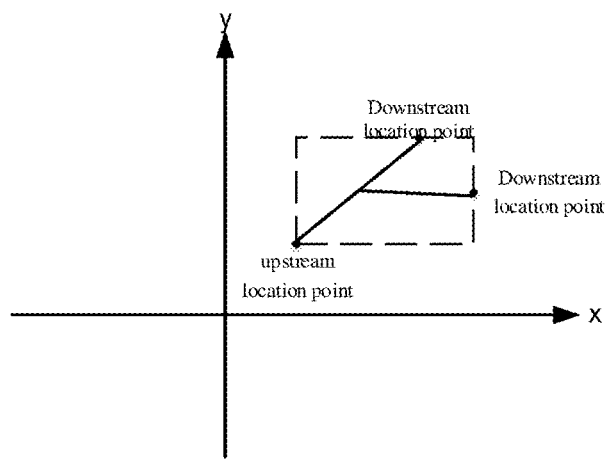
FIG. 5 shows a schematic diagram of determining a minimum containing rectangle (MCR) determined based on three points in a two-dimensional space according to the present disclosure.

FIG. 5 shows a schematic diagram of determining a minimum containing rectangle based on three points in a two-dimensional space according to the present disclosure. Following a similar method, a minimum containing cuboid is determined in the three-dimensional space based on three location points and one seed point.

Step S303: computing the centerline and the radius of the parent artery based on the seed point and location points.

Extraction of the parent artery centerline is crucial to segment the intracranial aneurysm. The inscribed circles in the parent artery lumen included in the cropped local image are computed point by point along the parent artery, where the connecting line between the circle center of the largest inscribed circle and the location point serves as the centerline of the parent artery, and the radius of the largest inscribed circle serves as the radius of the parent artery at the point.

Step 304: reconstructing the parent artery based on the centerline and the radius of the parent artery.

To effectively segment the aneurysm, it is needed to reconstruct the parent artery. Based on the centerline and the radius of the parent artery, with the point on the centerline as the spherical center and the radius at the point as the radius, the parent artery surface is generated point by point along the centerline to reconstruct the parent artery.

Step S305: segmenting the resulting complete aneurysm image using the parent artery to obtain the segmented aneurysm image.

The parent artery is reconstructed using the centerline; the resulting complete aneurysm image is segmented using the reconstructed parent artery; in this way, segmentation of the parent artery and aneurysm is implemented to obtain the segmented aneurysm image.

Step S306: performing region growing based on the seed point and the segmented aneurysm image to obtain the segmented aneurysm image.

The segmented aneurysm image has noises such as unclear boundaries; therefore, the segmented aneurysm image needs to be further processed so as to remove the noisy factors to obtain a clean and complete aneurysm image. The resulting segmented aneurysm image is a binary image; therefore, a communicating aneurysm image is obtained with the seed point as the growing point using the method of region growing, finally obtaining a segmented complete aneurysm image.

Step 103: measuring morphological parameters of the intracranial aneurysm image.

The resulting segmented complete intracranial aneurysm may be subjected to measurement of morphological parameters. To facilitate presentation, the segmented intracranial aneurysm image needs to be subjected to surface reconstruction.

Figure 6:
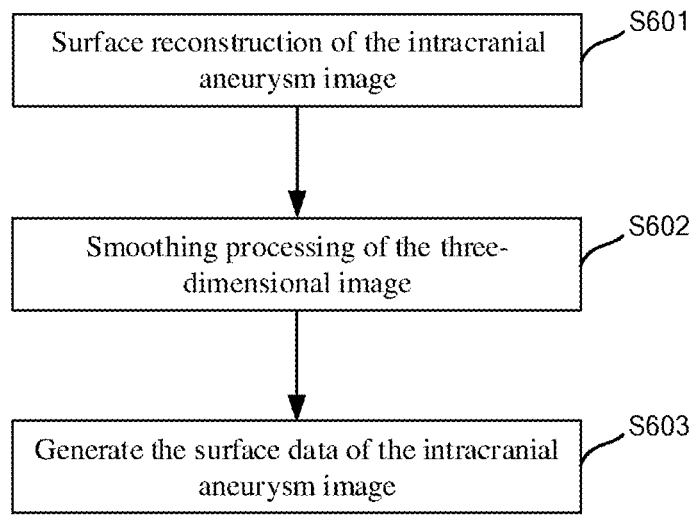
FIG. 6 shows a flow diagram of surface reconstruction of an intracranial aneurysm image according to the present disclosure.

FIG. 6 shows a flow diagram of surface reconstruction of the intracranial aneurysm image according to the present disclosure.

Step 601: reconstructing the surface of the intracranial aneurysm image.

The MC algorithm (MarchingCubes) is adopted herein to implement three-dimensional surface reconstruction. The basic idea of the MC algorithm is to layer a three-dimensional volume data space into small cubes of regular shapes. The eight vertexes of these small cubes are formed by the four pixel points on respective adjacent layers. By processing these small cubes one by one, cubes intersected with isosurfaces are sort out; the intersection points between the isosurfaces and the edges of the small cubes are calculated out by interpolation; finally, based on the relative positions between the isosurfaces and the intersection points, these points are connected according to a certain manner to approximate the isosurfaces. The 3D surface reconstruction is implemented by programming using the 3D visualization toolkit (VTK).

Step 602: performing smoothing processing using a windowed Sinc function.

The three-dimensional surface reconstructed with the MC algorithm has such issues that the surface seaming treatment is poor and the data are imprecise; therefore, smoothing processing is needed.

Step 603: obtaining surface data of the intracranial aneurysm image.

By smoothing processing the three-dimensional reconstruction with the MC algorithm, the surface data of the intracranial aneurysm image are obtained.

The morphological parameters of the intracranial aneurysm include aneurysm neck, aneurysm diameter, aneurysm height, aneurysm width, aneurysm inflow angle, and aneurysm volume. Particularly, how to compute the center of the aneurysm neck is key to measure the morphological parameters of the intracranial aneurysm.

Figure 7:
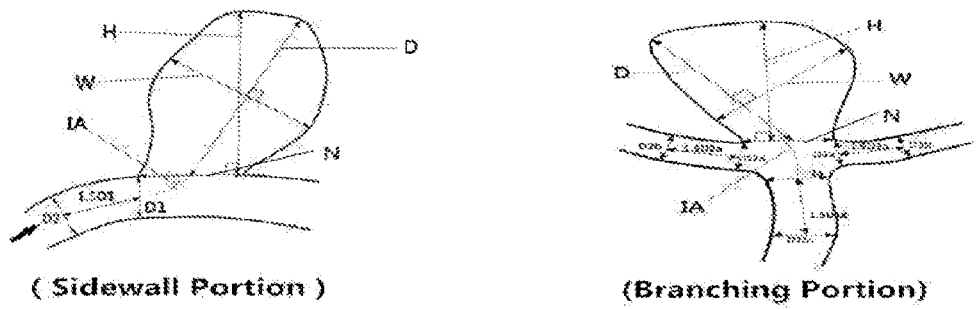
FIG. 7 shows a schematic diagram of definitions of morphological parameters of an aneurysm according to the present disclosure.

FIG. 7 shows a schematic diagram of defining morphological parameters of an aneurysm according to the present disclosure. The morphological parameters specifically include the following:

D (aneurysm diameter): the size of the aneurysm, which is the maximum distance from a point on the aneurysm dome to the middle point of the aneurysm neck;

H (aneurysm height): the maximum vertical length of the connecting line from a point on the aneurysm dome to the aneurysm neck;

W (aneurysm width): the maximum distance perpendicular to the aneurysm long diameter;

IA (inflow angle): the included angle between the diameter of the aneurysm and the central axis of the parent artery;

PV (diameter of the parent artery): Sidewall Portion: PV=(D1+D2)/2;

Bifurcation Portion: PV=(D1+D2+D3)/3, Di=(Dia+Dib)/2 (i=1, 2, 3)

Figure 8:
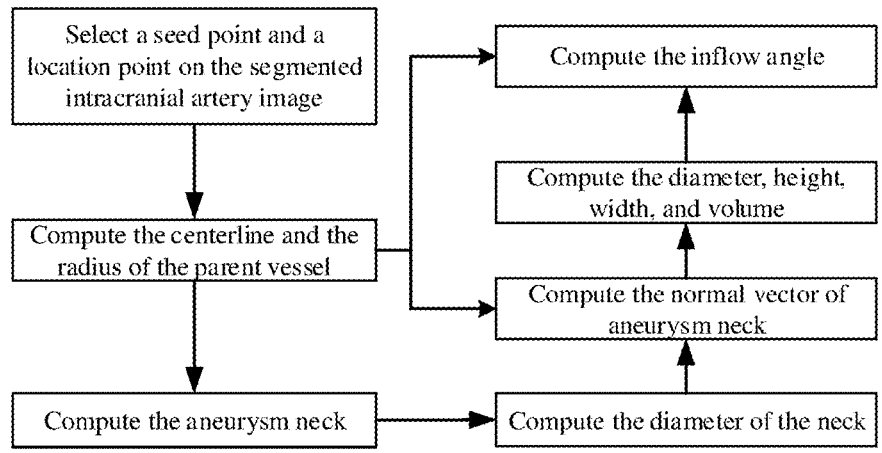
FIG. 8 shows a schematic diagram of measuring morphological parameters of an aneurysm according to the present disclosure.

FIG. 8 shows a schematic diagram of measuring morphological parameters of an aneurysm according to embodiments of the present disclosure. Specifically, the morphological parameters of the aneurysm are measured based on the following idea:

In the visualization toolkit VTK, the intersection between the aneurysm surface and the vessel surface should be actually intersected, without inclusion or overlap; therefore, it is needed to dilate the aneurysm surface data to realize actual intersection and obtain an intersection line. Upon expansion, the surface data of the entire aneurysm are dilated along three coordination directions. The dilated aneurysm surface is intersected with the original vessel surface, wherein the intersection is the aneurysm neck.

Computing the spatial geometric center of the point set based on the point set of the aneurysm neck: with the geometric center as the neck center of the aneurysm (wherein the geometric center might not be on the aneurysm), computing the minimum distance (denoted as $d_{min}$) between the geometric center and the aneurysm boundary; then computing the mean value of the distances between the points on the neck and the neck center; wherein the distance mean value is used as the neck radius, and the neck diameter is twice the neck radius.

Computing the normal vector of the neck: determining the center point of the shortest path along the centerline of the parent artery, wherein the connecting line between the center point of the path and the center point of the neck is the normal vector of the neck.

Computing the aneurysm height: projecting, on the normal vector of the neck, the connecting lines between points on the aneurysm and the center point of the neck, wherein the maximum value among the projections is used as the computed height value of the aneurysm; if the center point of the neck is inside the aneurysm, the computed height value serves as the height of the aneurysm; if the center point of the neck is outside the aneurysm, a result of the computed height value minus the $d_{min}$ serves the aneurysm height.

Computing the aneurysm diameter: finding the maximum value among the connecting lines between points on the aneurysm and the center point of the neck as the computed diameter value of the aneurysm; if the center point of the neck is located inside the aneurysm, the computed diameter value is the aneurysm diameter; if the center point of the neck is outside the aneurysm, the result of the computed diameter value minus the $d_{min}$ is the aneurysm diameter.

Computing the aneurysm width: first, computing the length of the connecting line between any two points on the aneurysm image perpendicular to the aneurysm diameter direction, wherein the maximum distance value is the aneurysm width.

Computing the aneurysm volume: first, counting the number of pixel points in the aneurysm image, and then using the product of the number of pixel points and the voxel as the volume of the aneurysm.

Computing the aneurysm inflow angle: first, computing a point on the centerline corresponding to the upstream location point on the centerline of the parent artery, and using the included angle between the connecting line between the point and the center point of the path and the aneurysm diameter as the aneurysm inflow angle.

Figure 9:
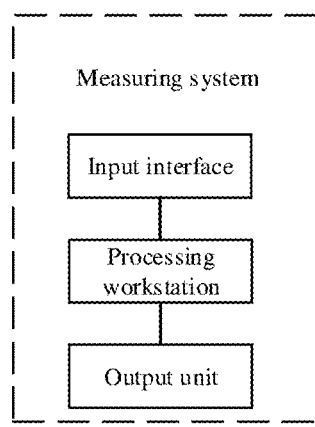
FIG. 9 shows a schematic diagram of a system for measuring morphological parameters of an aneurysm according to the present disclosure.

FIG. 9 shows a system for measuring morphological parameters of an aneurysm image according to the present disclosure. The system comprises:

an input interface configured for inputting three-dimensional DICOM data of DSA;

a processing workstation configured for measuring the morphological parameters of the intracranial aneurysm image; and an output unit configured for outputting measurements of the morphological parameters of the intracranial aneurysm image.

What have been described above are preferred embodiments of the present disclosure. The other embodiments fall within the scope of the appended claims. In some cases, the actions or steps disclosed in the claims may be executed according to a sequence different from those disclosed in the embodiments but may still achieve a desired result. Additionally, it is not compulsory for to follow the specific sequence or continuous sequence as illustrated in the drawings to achieve the desired result. In some embodiments, multi-task processing or concurrent processing is optional or likely beneficial.

Respective embodiments in the specification are described in a progressive manner, and same or similar parts between various embodiments may be referenced to each other, while each embodiment focuses on differences from other embodiments. Particularly, for an apparatus embodiment, an electronic device embodiment, and a non-volatile computer storage medium embodiment, because they are basically similar to the method embodiments, they are not detailed here and may refer to the depictions in the corresponding method embodiments.

The apparatus, electronic device, and non-volatile computer storage medium provided in the embodiments of the present disclosure correspond to the method; therefore, the apparatus, electronic device, and non-volatile computer storage medium also have beneficial effects of the corresponding method. As the beneficial effects of the method have been illustrated in detail, they will not be detailed here.

In 1990s, improvement of a technology may be apparently differentiated into hardware improvement (e.g., improvement of a circuit structure of a diode, a transistor, a switch, etc.) or software improvement (e.g., improvement of a method process). However, with development of technology, currently improvement of many method processes may be regarded as direct improvement to a hardware circuit structure. Designers always program an improved method process into a hardware circuit to obtain a corresponding hardware circuit structure. Therefore, it is improper to allege that improvement of a method process cannot be implemented by a hardware entity module. For example, a programmable logic device (PLD) (such as a field programmable gate array FPGA) is such an integrated circuit, a logic function of which is determined by programming a corresponding device. A designer may integrate a digital system on a piece of PLD by programming, without a need of engaging a chip manufacturer to design and fabricate a dedicated integrated circuit chip. Moreover, currently, in replacement of manual fabrication of an integrated circuit chip, this programming is mostly implemented by a logic compiler, which is similar to a software compiler used when developing and writing a program. To compile the previous original code, a specific programming language is needed, which is referred to as a hardware description language (HDL). Further, there are more than one HDLs, e.g., ABEL (Advanced Boolean Expression Language), AHDL(Altera Hardware Description Language), Confluence, CUPL (Cornell University Programming Language), HDCal, JHDL (Java Hardware Description Language), Lava, Lola, MyHDL, PALASM, RHDL (Ruby Hardware Description Language), among which, VHDL (Very-High-Speed Integrated Circuit Hardware Description Language) and Verilog are used most prevalently. Those skilled in the art should also understand that a hardware circuit for a logic method process can be easily implemented by subjecting, without much efforts, the method process to logic programming using the above hardware descriptive languages into an integrated circuit.

A controller may be implemented according to any appropriate manner. For example, the controller may adopt manners such as a microprocessor or processor and a computer readable medium storing computer readable program codes (e.g., software or firmware) executable by the (micro) processor, a logic gate, a switch, an application specific integrated circuit (ASIC), a programmable logic controller, and an inlaid microcontroller. Examples of the controller include, but are not limited to, the following microcontrollers: ARC 625D, Atmel AT91S AM, Microchip PIC18F26K20 and Silicone Labs C8051F320. The memory controller may also be implemented as part of the control logic of the memory. Those skilled in the art may further understand that besides implementing the controller by pure computer readable program codes, the method steps may be surely subjected to logic programming to enable the controller to implement the same functions in forms of a logic gate, a switch, an ASIC, a programmable logic controller, and an inlaid microcontroller, etc. Therefore, the controller may be regarded as a hardware component, while the modules for implementing various functions included therein may also be regarded as the structures inside the hardware component. Or, the modules for implementing various functions may be regarded as software modules for implementing the method or structures inside the hardware component.

The system, apparatus, module or unit illustrated by the embodiments above may be implemented by a computer chip or entity, or implemented by a product having a certain function. A typical implementation device is a computer. Specifically, the computer for example may be a personal computer, a laptop computer, a cellular phone, a camera phone, a smart phone, a personal digital assistant, a media player, a navigation device, an email device, a game console, a tablet computer, a wearable device, or a combination of any of these devices.

To facilitate description, the apparatuses above are partitioned into various units by functions to describe. Of course, when implementing one or more embodiments of the present application, functions of various units may be implemented in one or more pieces of software and/or hardware.

Those skilled in the art should understand that the embodiments of the present disclosure may be provided as a method, a system, or a computer program product. Therefore, the embodiments of the present disclosure may adopt a form of complete hardware embodiment, a complete software embodiment, or an embodiment combining software and hardware. Moreover, the embodiments of the present disclosure may adopt a form of a computer program product implemented on one or more computer-adaptable storage media including computer-adaptable program code (including, but not limited to, a magnetic disc memory, CD-ROM, and optical memory, etc.).

The present disclosure is described with reference to the flow diagram and/or block diagram of the method, apparatus (system) and computer program product according to the embodiments of the present disclosure. It should be understood that each flow and/or block in the flow diagram and/or block diagram, and a combination of the flow and/or block in the flow diagram and/or block diagram, may be implemented by computer program instructions. These computer program instructions may be provided to a processor of a general-purpose computer, a dedicated computer, an embedded processor, or other programmable data processing device to generate a machine, such that an apparatus for implementing the functions specified in one or more flows of the flow diagram and/or one or more blocks in the block diagram is implemented via the computer or the processor of other programmable data processing device.

These computer program instructions may also be stored in a computer readable memory that may boot the computer or other programmable data processing device to work in a specific manner such that the instructions stored in the computer readable memory to produce a product including an instruction apparatus, the instruction apparatus implementing the functions specified in one or more flows of the flow diagram and/or in one or more blocks in the block diagram.

These computer program instructions may be loaded on the computer or other programmable data processing device, such that a series of operation steps are executed on the computer or other programmable device to generate a processing implemented by the computer, such that the instructions executed on the computer or other programmable device provide steps for implementing the functions specified in one or more flows of the flow diagram and/or one or more blocks in the block diagram is implemented via the computer or the processor of other programmable data processing device.

In a typical configuration, the computing device includes one or more processors (CPUs), an input/output interface, a network interface, and a memory.

The memory may include a non-permanent memory in a computer readable medium, a random access memory (RAM) and/or a non-volatile memory, e.g., a read-only memory (ROM) or a flash memory (flash RAM). The memory is an example of a computer readable medium.

The computer readable memory includes a permanent type, non-permanent type, a mobile type, and a non-mobile type, which may implement information storage by any method or technology. The information may be a computer-readable instruction, a data structure, a module of a program or other data. Examples of the memory mediums of the computer include, but are not limited to, a phase-change RAM (PRAM), a static random access memory (SRAM), a dynamic random access memory (DRAM), other type of random access memory (RAM), a read-only memory (ROM), an electrically erasable programmable read only memory (EEPROM), a flash memory body or other memory technology, a CD-ROM (Compact Disc Read—Only Memory), a digital multi-function optical disc (DVD) or other optical memory, a magnetic cassette type magnetic tape, a magnetic tape disc memory, or other magnetic storage device or any other non-transmission medium which may be configured for storing information to be accessed by a computing device. Based on the definitions in the specification, the computer readable medium does not include a transitory media, e.g., a modulated data signal and a carrier.

It needs also be noted that the terms "include," "comprise" or any other variables intend for a non-exclusive inclusion, such that a process, a method, a product or a system including a series of elements not only includes those elements, but also includes other elements that are not explicitly specified or further includes the elements inherent in the process, method, product or system. Without more restrictions, an element limited by the phase "including one . . . " does not exclude a presence of further equivalent elements in the process, method, product or system including the elements.

The present application may be described in a general context of the computer-executable instruction executed by the computer, for example, a program module. Generally, the program module includes a routine, a program, an object, a component, and a data structure, etc., which executes a specific task or implements a specific abstract data type. The present application may be practiced in a distributed computing environment, in which a task is performed by a remote processing device connected via a communication network. In the distributed computing environment, the program module may be located on a local or remote computer storage medium, including the memory device.

Respective embodiments in the specification are described in a progressive manner, and same or similar parts between various embodiments may be referenced to each other, while each embodiment focuses on differences from other embodiments. Particularly, for a system embodiment, because it is substantially similar to the method embodiment, it is described relatively simply. Relevant parts may refer to the method embodiments.

What have been described above are only preferred embodiments of the present disclosure, not for limiting the present disclosure; to those skilled in the art, the present disclosure may have various alterations and changes. Any modifications, equivalent substitutions, and improvements within the spirit and principle of the present disclosure should be included within the protection scope of the present disclosure.

We claim:

1. A method for measuring morphological parameters of an intracranial aneurysm image, comprising:
   segmenting an intracranial parent artery image from three-dimensional Digital Imaging and Communications in Medicine (DICOM) data of Digital Subtraction Angiography (DSA);
   segmenting the intracranial aneurysm image on the intracranial parent artery image, wherein the segmenting the intracranial aneurysm image on the intracranial parent artery image comprises computing the centerline and radius of the parent artery on the intracranial parent artery image to segment the intracranial aneurysm image;
   generating an aneurysm neck using the segmented intracranial aneurysm image, wherein the geometric center of the aneurysm neck is considered as the center of the aneurysm neck; and
   measuring morphological parameters of the intracranial aneurysm image based on the center of the aneurysm neck.

2. The method according to claim 1, wherein the segmenting an intracranial parent artery image from three-dimensional DICOM data of DSA specifically comprises:
   automatically selecting a seed point on the three-dimensional DICOM data of the DSA to segment the intracranial parent artery image.

3. A system for measuring morphological parameters of an intracranial aneurysm image, comprising:
   an input interface configured for inputting three-dimensional DICOM data of DSA;
   a processing workstation configured for measuring the morphological parameters of the intracranial aneurysm image, wherein the measuring the morphological parameters of the intracranial aneurysm image specifically comprises:
   segmenting an intracranial parent artery image from the three-dimensional DICOM data of DSA:
   segmenting the intracranial aneurysm image on the intracranial parent artery image, wherein the segmenting the intracranial aneurysm image on the intracranial parent artery image comprises computing the centerline and radius of the parent artery on the intracranial parent artery image to segment the intracranial aneurysm image;
   generating an aneurysm neck using the segmented intracranial aneurysm image, wherein the geometric center of the aneurysm neck is considered as the center of the aneurysm neck; and
   measuring the morphological parameters of the intracranial aneurysm image based on the center of the aneurysm neck; and
   an output unit configured for outputting measurements of the morphological parameters of the intracranial aneurysm image.

4. The system according to claim 3, wherein the segmenting an intracranial parent artery image from three-dimensional DICOM data of DSA specifically comprises:
    automatically selecting a seed point on the three-dimensional DICOM data of the DSA to segment the intracranial parent artery image.

* * * * *